United States Patent [19]
Houghton et al.

[11] Patent Number: 4,970,895
[45] Date of Patent: Nov. 20, 1990

[54] SYSTEM AND METHOD FOR THE DETERMINATION OF CERTAIN PHYSICAL CHARACTERISTICS OF SHEET MATERIALS.

[75] Inventors: Paul J. Houghton; Lee M. Chase, both of Los Gatos; John D. Goss, San Jose; Michael K. Norton, Los Gatos; Leonard M. Anderson, San Jose, all of Calif.

[73] Assignee: Measurex Corporation, Cupertino, Calif.

[21] Appl. No.: 494,906

[22] Filed: Mar. 9, 1990

Related U.S. Application Data

[63] Continuation of Ser. No. 345,618, May 1, 1989, abandoned, and a continuation-in-part of Ser. No. 730,406, May 2, 1985, abandoned, Ser. No. 345,618, , which is a continuation-in-part of Ser. No. 220,415, Jul. 18, 1988, abandoned, which is a continuation of Ser. No. 920,107, Oct. 6, 1986, abandoned.

[51] Int. Cl.$^5$ .............................................. G01L 5/04
[52] U.S. Cl. ........................................ 73/159; 364/471
[58] Field of Search ...................... 73/159, 840, 862.48, 73/789, 826; 364/471

[56] References Cited

U.S. PATENT DOCUMENTS

| | | |
|---|---|---|
| 2,674,127 | 4/1954 | Garrett . |
| 2,809,519 | 10/1957 | Kaestner ................................ 73/159 |
| 2,834,203 | 5/1958 | Sampson . |
| 2,909,660 | 10/1959 | Alexander . |
| 2,966,792 | 1/1961 | Di Pieri . |
| 3,204,454 | 9/1965 | Friman . |

(List continued on next page.)

FOREIGN PATENT DOCUMENTS

| | | |
|---|---|---|
| 751614 | 10/1954 | Fed. Rep. of Germany . |
| 1008503 | 5/1957 | Fed. Rep. of Germany . |
| 1012760 | 7/1957 | Fed. Rep. of Germany . |
| 1012760 | 7/1957 | Fed. Rep. of Germany . |
| 2054505 | 11/1969 | Fed. Rep. of Germany . |
| 475609 | 6/1979 | Switzerland . |
| 934328 | 8/1963 | United Kingdom ................ 73/159 |
| 1328158 | 8/1973 | United Kingdom . |

OTHER PUBLICATIONS

Foxboro Bulletin, Test Results are Automatically Recorded, vol. 10–5, Aug. 1964.
"A High Temperature Four Point Bending Machine for Testing Thin Sheets of Materials", J. L. Martin, et al., Office National d'Estudes et de Recherche Aeropatiales Dec. 29, 1970.
Commonly assigned related U.S. patent application Serial No. 195,364.
Commonly assigned related U.S. patent application Serial No. 056,332.
"On-Line Measurement of Strength Characteristics of a Moving Sheet", M. G. Lu, TAPPI, vol. 58, No. 6, pp. 80–81, Jun. 1975.
"Control in the Paper Industry Up to the Minute", E. J. Kompass, Control Engineering, vol. 25, No. 12, pp. 44–46, Dec. 1978.
Checkline Brochure for Checkline Type DTM Microprocessor-Controlled Tensiometer.

*Primary Examiner*—Jerry W. Myracle
*Attorney, Agent, or Firm*—Spensley Horn Jubas & Lubitz

[57] ABSTRACT

A sensor is disclosed for sensing a physical property of a sheet material. The sensor includes a mechanism for supporting one side of the sheet along the periphery of a defined region and a mechanism for forcibly deflecting the sheet into the unsupported center of the defined region. A transducer may also be incorporated to sense the force required to deflect the sheet into the unsupported region and/or the distance that the sheet is deflected into the unsupported region. The sensor may be operatively coupled to a computer programmed to determine a physical property of the sheet based upon the sensed force and/or distance, such as the sheet failure strength.

56 Claims, 7 Drawing Sheets

U.S. PATENT DOCUMENTS

| | | | |
|---|---|---|---|
| 3,474,668 | 10/1967 | Mangan . | |
| 3,552,203 | 1/1971 | Freeh | 73/159 |
| 3,619,360 | 11/1971 | Persik . | |
| 3,621,259 | 11/1971 | Boissevain . | |
| 3,622,448 | 2/1972 | Adams et al. . | |
| 3,649,444 | 5/1972 | Futch . | |
| 3,711,688 | 1/1973 | Stout et al. | 235/151.1 |
| 3,718,037 | 2/1973 | Stringer | 73/159 X |
| 3,738,151 | 6/1973 | Giunta et al. | 73/1 B |
| 3,757,122 | 9/1973 | Bossen et al. . | |
| 3,793,878 | 2/1974 | Brunton . | |
| 3,822,588 | 7/1974 | Knight et al. | 73/81 |
| 3,823,371 | 5/1972 | Lippke . | |
| 3,886,036 | 5/1975 | Dahlin . | |
| 4,068,385 | 1/1978 | Mitzel | 33/143 L |
| 4,080,656 | 3/1978 | Jonsson | 364/471 |
| 4,221,577 | 9/1981 | Baum et al. | 73/597 |
| 4,374,703 | 2/1983 | Lebeau et al. | 162/253 |
| 4,453,404 | 6/1984 | Powell et al. | 73/159 |
| 4,587,855 | 5/1986 | Yamada | 73/862.48 |
| 4,674,310 | 6/1987 | Ginzberg | 73/159 X |
| 4,678,915 | 7/1987 | Dahlquist | 250/358.1 |

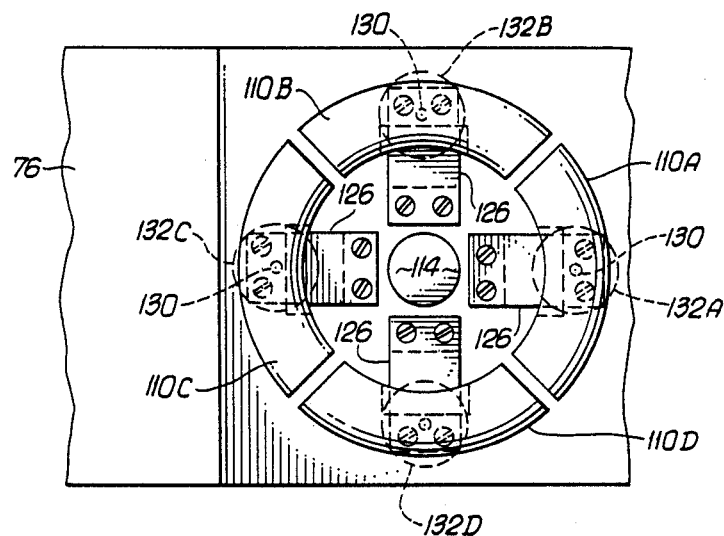
Fig. 6
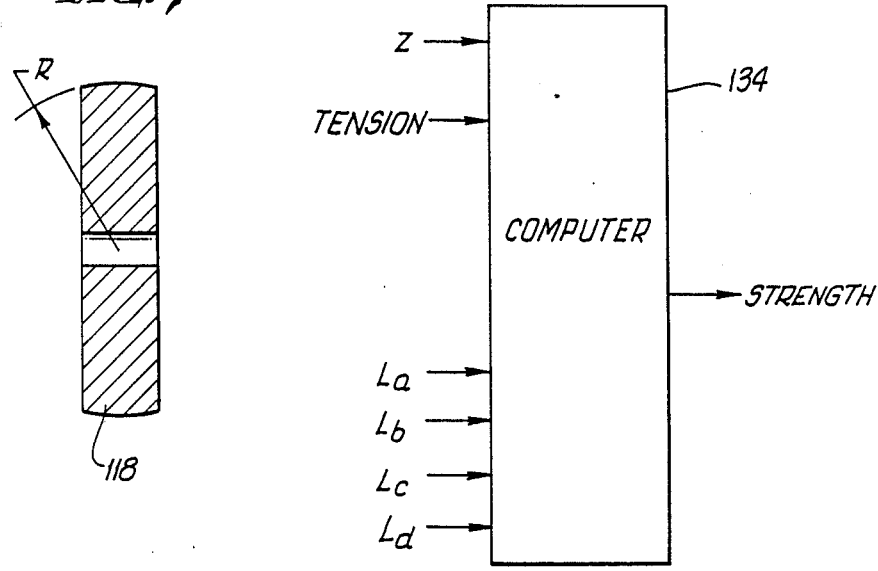
Fig. 7
Fig. 8

SYSTEM AND METHOD FOR THE DETERMINATION OF CERTAIN PHYSICAL CHARACTERISTICS OF SHEET MATERIALS.

This is a continuation of application Ser. No. 07/345,618 filed on May 1, 1989, which is a continuation-in-part application of prior application Ser. No. 07/220,415, filed July 18, 1988, which is a continuation of application Ser. No. 06/920,107, filed Oct. 16, 1986, now abandoned. Application Ser. No. 07/345,617 is also a continuation-in-part of Application Ser. No. 06/730,406, filed May 2, 1985, now abandoned.

FIELD OF THE INVENTION

The present invention concerns a system and method for measuring the strength and other characteristics of a sheet such as paper while the sheet is being produced.

BACKGROUND OF THE INVENTION

Among the critical characteristics of paper and other sheet materials which are important to both manufacturers and users is strength. Many different methods for measuring strength have been proposed in the past, but virtually all suffer from a great disadvantage, namely, the tests are destructive and cannot be used "on line". A number of standardized tests have been devised to provide a basis for specifications by which paper can be bought and sold, and these tests provide arbitrary but nevertheless useful strength indices for comparing the strengths of various papers. Unfortunately, all are destructive, and none can be used "on-line". The more common tests are a standardized tensile test, the so-called "STFI" compressions test, and the "burst pressure" or "Mullen" test. Pierce strength is also an important strength parameter.

In the standard tensile test, a strip of paper is held between two clamps and loaded in tension at a predetermined rate. The loading at failure is taken to be a measure of the tensile strength of the paper. There are a number of standardized procedures which have been adopted to perform this test, e.g., TAPPI Standard T404os-76 and ASTM Standard D828.

The "STFI" compression test for heavy papers is a standardized test whose procedure has been established by the Swedish Technical Forest Institute as specified by the identifiers: Scan P46 Column 83. In this test a strip of the paper to be tested is held between a pair of clamps which are moved together at a fixed rate while the compressive force is monitored. "Rupture" occurs when the compressive force passes a peak and begins to drop. The force at "rupture" is taken as the compressive strength of the paper. Other standard specifications for this test are, e.g., TAPPI 7818os-76 and ASTM D1164.

The strengths of papers as measured by the foregoing tests typically have different values depending on whether the test strip is cut in the "machine direction" or the "cross direction". The "machine direction" is generally defined by the direction of travel of the sheet when it is being manufactured by the papermaking machine. The "cross direction" is generally defined as the two directions in the plane of the sheet perpendicular to the machine direction.

A "Mullen" or burst pressure test is conducted by clamping a sample of the paper between two circular clamping rings having a specified standard inside diameter, and building up pressure on one side of the paper until the paper bursts (using a rubber diaphragm and liquid pressure). The pressure required to burst the paper is known as the "burst pressure" and is the figure often used to specify the required strength. Common burst pressure specifications are TAPPI 403os-76 and ASTM D774.

On-line determination of paper strength during the manufacture of paper can aid in producing paper which can meet the specified strength requirements. Needless to say, however, none of the above-mentioned tests lend themselves to use in connection with the continuous measurement of paper strength. Nevertheless, because of their widespread popularity, it is desirable that any method used to measure the strength of paper provides results which correlate with one of the recognized standard tests.

U.S. Pat. No. 4,291,577 teaches a system for measuring the strength of paper as it is being produced. The patent provides for measurement of the velocity of ultrasonic waves through the moving paper sheet. Based upon the velocity, the strength of the paper is determined.

The patent teaches a device having two wheels which are spaced apart from one another and which roll along the moving paper sheet or "web". The first wheel contains a transducer in the form of a rectangular button mounted on the periphery of the wheel so that as the wheel rotates the button periodically contacts the paper. With each revolution of the wheel, when the transducer contacts the paper, it receives an electrical signal from a signal generator and imparts a mechanical signal to the paper. The second wheel contains a receiving transducer substantially the same as the transmitting transducer, which also is mounted on the periphery of the wheel and occupies a small percentage of the total circumference of the wheel. The receiving transducer contacts the paper once each revolution of the wheel and receives the signal from the transmitter by picking up the ultrasound signal from the paper and converting it to an electrical signal. The system also includes a position detector to monitor the rotational position of the first wheel and to trigger the firing of the ultrasound pulse by the transmitter when the wheel is in a predetermined position. The rotation of the receiving wheel is coordinated with the transmitting wheel so that the receiving transducer is in contact with the paper at the appropriate time to receive the transmitted signal. The signal from the receiving transducer is transmitted to a metering and recording apparatus which measures the velocity of the ultrasonic waves.

Unfortunately, the system described in the patent has a number of disadvantages. Since the transmitting and the receiving transducer each contact the paper during only a small percentage of the total rotation of the wheels, the rotation of the wheels must be carefully synchronized and the transmission of the pulse must be carefully timed so that the pulse is received by the transmitter when it is in contact with the paper. Furthermore, since the transmitter and the receiver are only in contact with the paper for a small percentage of the total rotation of the wheels, a substantial portion of the paper is not subject to velocity measurement.

SUMMARY OF THE INVENTION

By its nature, a measurement of the strength of paper or other sheet materials is destructive. Fortunately, however, we have found that the strength, i.e., the failure strength of a sheet, is related to factors which can be measured on a continuous basis by non-destructive means.

Certain embodiments of the present invention provide a system for non-destructively determining the strength of paper and like sheet materials being manufactured. The major factors which influence the strength of paper, e.g., its basis weight and thickness, also affect the elastic modulus and bending stiffness of the sheet. We have found that these latter factors can be sensed in a sheet under tension in such a way that the actual strength of a sheet can be determined by computation from the output of the sensor. The preferred form of strength sensor used senses a characteristic of the paper which will be referred to as "elastic modulus" since the characteristic is related to the modulus, but is not actually a measure of the elastic modulus of the sheet itself. Quotation marks are used around the term "elastic modulus" to indicate that the function, while related to the elastic modulus is really an empirically derived factor which depends on other characteristics such as bending stiffness also.

The "elastic modulus" sensor in one embodiment of the present invention uses a paper web contact means or support ring which is split into four segments, each occupying approximately 90 degrees of the ring circle. Each segment is supported on a pair of leaf springs and a sensing device such as a load cell so that first means such a free running wheel acting on the paper in the center of the ring will deflect the paper and result in an output from each of the four load cells, with the output level being dependent in part on paper characteristics. The four segments may be aligned so that two of the segments are sensitive to machine direction characteristics of the paper and two are sensitive to cross direction characteristics. A free running wheel pressing on the paper at the center of the web support ring provides the force which is transmitted to each load cell.

A computer accepts the outputs of each of the load cells and calculates the paper strength using these signals in accordance with certain empirical equations which have been developed.

It should be understood that while references are made to specific standardized tests herein, the references are intended to be exemplary only and not limiting. The present invention can be utilized to provide determinations which correlate well with a wide variety of standardized tensile, compressive and burst pressure tests. Alternatively, the present invention can be utilized to provide an arbitrary index of strength which will allow comparisons of strength as between products independent of any existing standardized system.

In certain embodiments, the present invention provides a system and process or method for continuously measuring the strength of a moving sheet. Such a system may utilize the tension and elastic modulus of the sheet and also the velocity of the sheet to determine strength.

A clear understanding of the invention can be had by referring to the following detailed description of the presently preferred embodiments of the invention, together with the appended drawings.

BRIEF DESCRIPTION OF THE DRAWINGS

FIG. 6 is a top plan view of the portion of the lower gauge support member in the region of the sensing ring.

FIG. 7 is a fragmentary cross-sectional view of the sensing wheel.

FIG. 8 is a block diagram of the electronic portion of one embodiment of the invention.

DETAILED DESCRIPTION OF THE INVENTION

As an aid in understanding the invention, the papermaking process is briefly described with reference to FIG. 1. A more elaborate description is provided in U.S. Pat. No. 3,757,122 issued Sept. 4, 1973 and entitled "Basis Weight Gauging Apparatus, System and Method Using A Digital Count".

Figure 1:
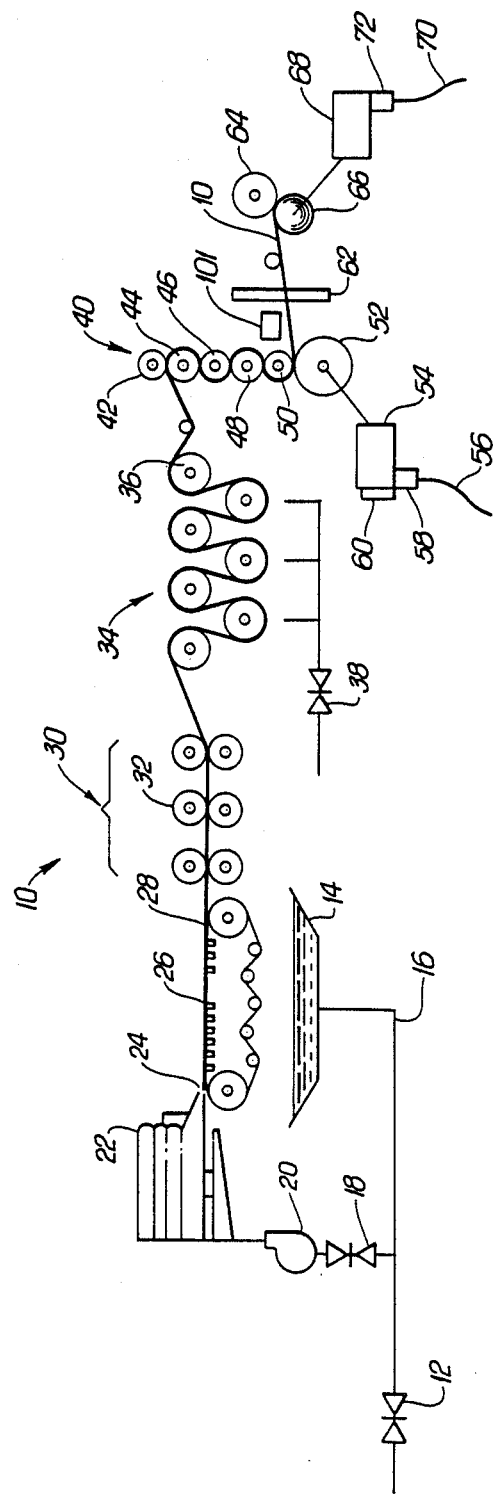
FIG. 1 is a schematic illustration of one embodiment of the present invention operating in connection with a papermaking machine.

With reference to FIG. 1, raw stock is supplied to paper machine 10 through stock valve 12. White water from collection reservoir 14 is drained by a line 16, mixed with raw stock and supplied through stream valve 18 and fan pump 20 to head box 22. The pulp and white water mixture jets from head box 22 through slice lip 24 on top of and parallel with wire 26. Water passes through wire 26 and is collected by reservoir 14. However, the majority of fiber is left behind to form a set sheet of paper 28.

After leaving wire 26, sheet 28 is passed through press 30 consisting of a plurality of rollers 32 which removes much of the water from sheet 28. Thereafter, the paper sheet 28 passes into a dryer section 34 consisting of a plurality of rollers 36 through which steam is supplied by a steam control valve 38. The steam heats the rollers 36 and consequently evaporates much of the water in the paper sheet 28 so that the paper emerging from dryer section 34 has the desired moisture content.

The paper then passes from dryer section 34 to a calender stack 40. The calender stack 40 includes a plurality of calender rollers 42, 44, 46, 48, 50 and 52. The bottom most roller, 52, is larger than the other rollers and is driven by a motor 54 which is powered by electricity from line 56. Electricity from line 56 is supplied to the motor 54 through an ammeter 58 which measures the current passing through line 56. A tachometer 60 is coupled to the motor 54 to measure the speed of the motor 54.

After leaving the calender rolls 50 and 52, the sheet passes through scanner 62 and is wound onto reel 64. The reel 64 is driven to rotate by a pope roll 66 which in turn is rotated by motor 68. The motor 68 receives electric current through line 70 and ammeter 72.

Figure 2:
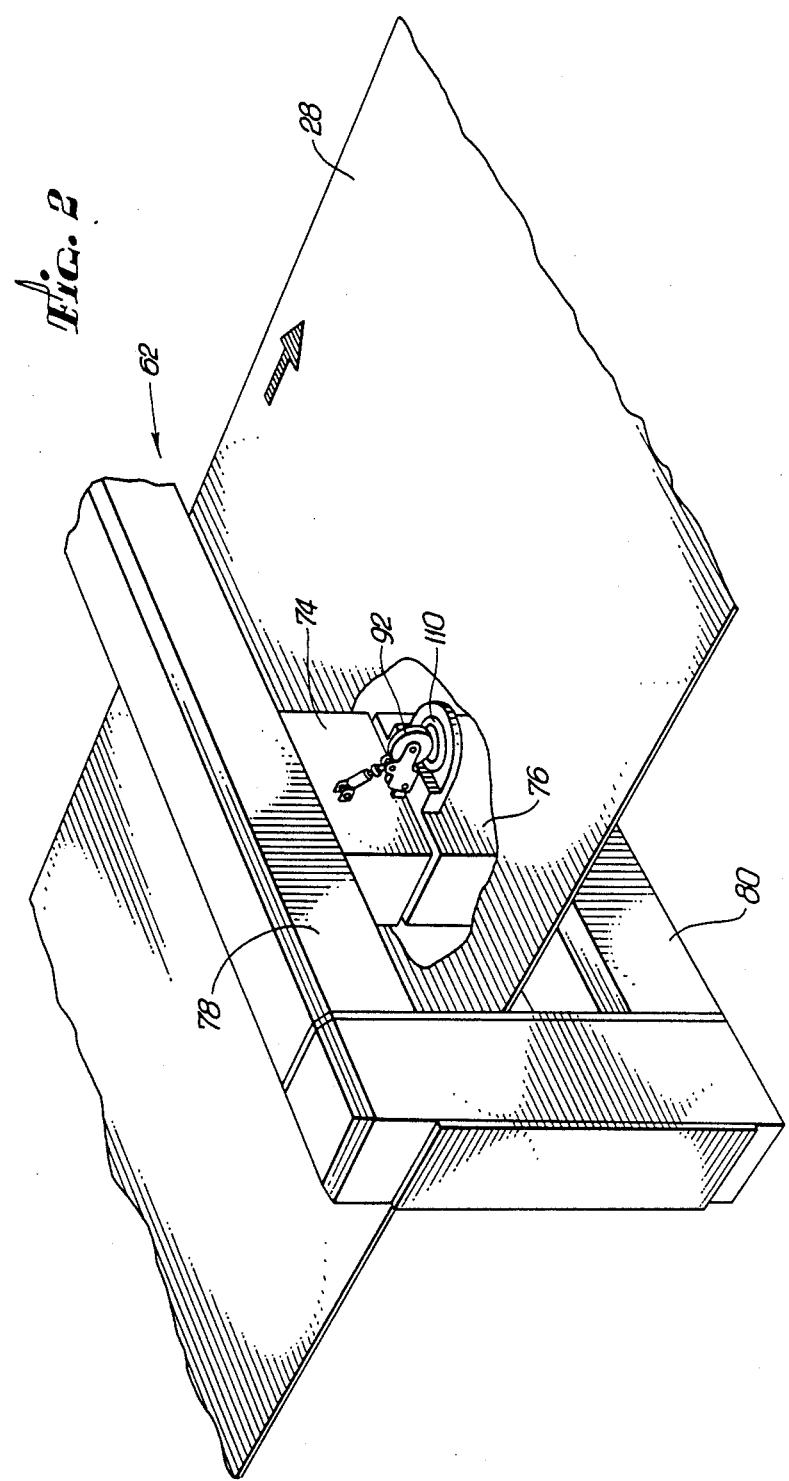
FIG. 2 is a perspective view of the sensing portion of the inventive apparatus as installed in a papermaking machine.

The scanner 62, best illustrated in FIG. 2, is conventional and will therefore not be discussed in detail herein. However, basically, the scanner 62 includes two heads or gauge support members, one 74 disposed above and the other 76 below the sheet of paper 28. The scanner 62 also includes a drive system (not shown) to cause the scanner heads 74, 76 to reciprocate back and forth across the moving sheet of paper 28. Further details of a scanner 62 can be ascertained from U.S. Pat. No. 3,621,259 titled "Sheet-Gauging Apparatus".

The present invention is most advantageously used to monitor the strength of the paper 28 after the final calendering operation, and before the paper is rolled up on the final reel 64 (FIG. 1). The windup motor 68 maintains a constant tension in the sheet 28 between the calander stack 40 and the reel 64. Since the strength of the paper 28 produced may vary across the sheet 28 as well as along the sheet 28, the present invention preferably, but not necessarily, involves the use of the previously mentioned scanning system 62, whereby the sensor mounted to the scanner heads 74, 76, scans across the width of the paper 28 while the paper 28 is being fed out of the calender stack 40 and into the reroll system. In this way the variations in strength, side to side, may be determined, as well as the strength of the paper 28 at each section along its length.

FIG. 2 shows such a scanning station 62 which, as noted above, is preferably located after the final calender rolls and before the reroll system. A web or sheet of paper 28 can be seen in FIG. 2 passing through the scanning station 62 between two transverse beams 78 and 80, on which are mounted upper and lower gauge support members 74, 76, with a cut out area so that the relationship between the gauge support members 74, 76 can be seen. A motor (not shown) within the scanning station 62 is coupled to, and drives the members 74, 76 back and forth across the width of the paper 28 in a continuous scanning motion, keeping them in alignment at all times.

The sensor used to detect the physical characteristic of the paper for ease of reference is called a strength sensor since it senses a physical characteristic which may be correlated to the sheet or paper strength. In the particular embodiments of the sensor shown, the characteristic may be sensed by detecting the force required to deflect the sheet a predetermined amount or by detecting the deflection of the sheet when subjected to a predetermined force. Both methods are within the broad scope of the invention. The strength sensor is carried on gauge supports 74, 76.

Figure 3:
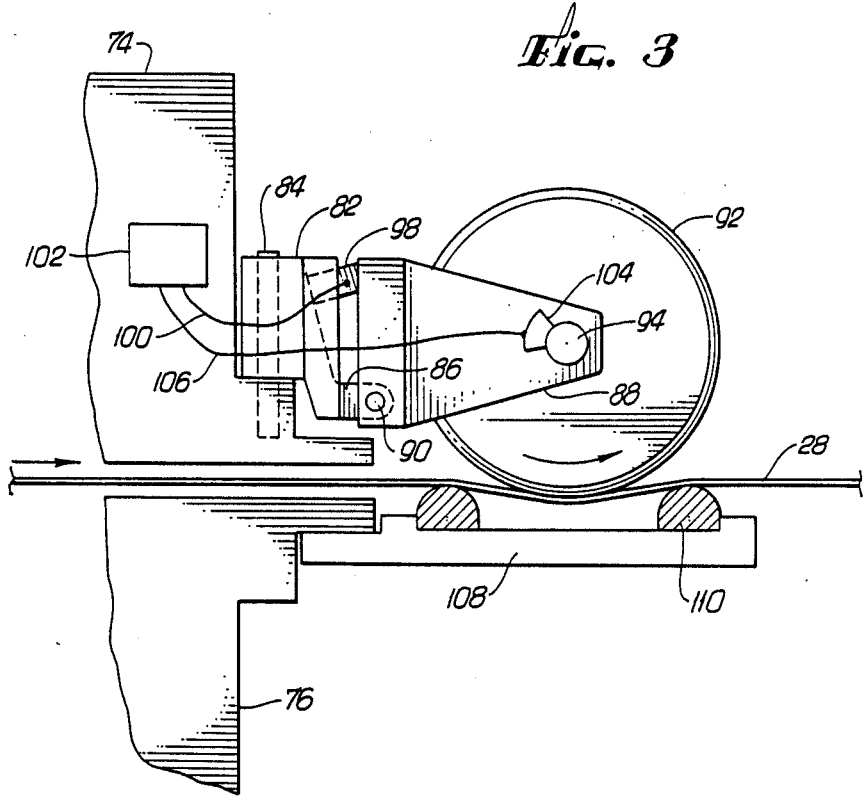
FIG. 3 is a schematic side illustration of one embodiment of the present invention
Figure 4:
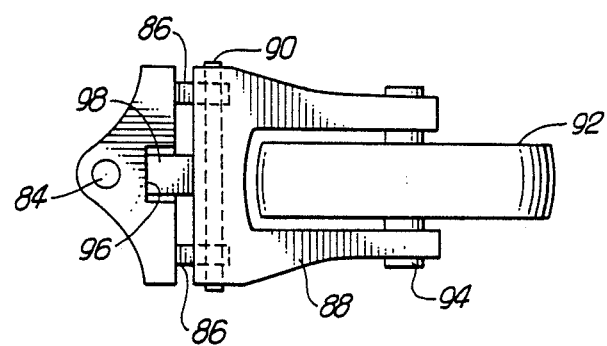
FIG. 4 is a top view of the apparatus of FIG. 3.

Turning now to FIGS. 3 and 4, there is shown part of an upper gauging head 74 and part of a lower gauging head 76. Both heads 74 and 76 are coupled to the scanner 62 so that they can be moved back and forth across the moving sheet of paper 28. A support member 82 is coupled to the upper gauge head 74 by pivot 84. The support member 82 includes two brackets 86 mounted at its lower end, and a U-shaped bracket 88 is coupled to the brackets 86 by pivot 90. Thus it can be seen that the U-shaped bracket 88 can rotate horizontally about pivot 84 and vertically about pivot 90.

A wheel 92 is mounted in the U-shaped bracket 88 by an axle 94 on bearings (not shown). Thus, the wheel 92 is free to rotate as indicated by the arrow and also to move upward and downward as the bracket 88 rotates about the pivot 90.

The support member 82 includes an indentation 96 adjacent the upper part of U-shaped bracket 88. A load cell 98 is coupled to the support member 82 in the indentation 96 and also to the bracket 88. The load cell 98 is a conventional device to measure the compressive force. Thus it can be seen that the load cell 98 measures the upward force on the wheel 92. The load cell 98 is coupled by line 100 to transmit signals to a computing system 102 mounted in the upper gauging head 74.

A tachometer 104 is coupled to the bracket 88 and to the axle 94 to measure the rate of rotation of the wheel 92 and generate a signal corresponding thereto. The signals from the tachometer 104 are conveyed to the computing system 102 by a line 106.

A support 108 is coupled to the lower gauging head 76, below the sheet 28, and sheet support member 110 is coupled to the support 108. The sheet support member 110 is substantially toroidal in shape and has a smooth, rounded upper surface.

In operation, the wheel 92 is mounted above the sheet of paper 28, and the sheet support member 110 is mounted directly below the wheel 92, and on the opposite side of the sheet of paper 28. The wheel 92 and sheet support member 110 are positioned so that the sheet 28 is in contact with the upper surface of the support member 110, and the wheel 92 pushes the paper in the center of the support member 110 downwardly a predetermined distance which in practice can be about 0.2–0.5 centimeters, and preferably about 0.4 centimeters, below the upper edge of the support member 110 for a support member 110 about 5 inches in diameter. Thus, increases and decreases in the tension and elastic modulus (i.e., the ratio of stress to strain in the paper) of the sheet 28 impart variable forces on the load cell 98. Higher sheet tension or higher elastic modulus results in higher force on the load cell 98. Also, the wheel 92 is caused to rotate as the sheet 28 moves. The computer 102 receives signals from the load cell 98 corresponding to the tension and elastic modulus in the paper and signals from the tachometer 104 corresponding to the velocity of the paper 28. The computing sytem 102 utilizes the data to determine the strength of the sheet of paper 28 as will be discussed in more detail hereinafter As the heads 74 and 76 scan across the sheet 28, the support member 82 and wheel 92 pivot slightly about pivot 84 so that the wheel 92 rolls smoothly on the sheet 28.

The computing system 102 receives signals from the ammeter 58 which measures the load on the motor 54 driving calendar roller 52. The load on motor 54 is representative of the average tension on the sheet of paper between roller 36 and the first calender stack roller 42. The computing system 102 also receives signals from the ammeter 72 which indicate the load on the motor 68 which in turn is representative of the tension on the sheet 28 between the calandar roller 52 and the pope roll 66. The computing system 102 also receives signals from tachometer 60 measuring the speed of motor 54, which is representative of the speed of the sheet of paper 28 as it passes over roller 52.

The computing system 102 utilizes the parameters discussed above to determined the strength of the paper 28 according to the following equation:

$$S = C\left[\frac{L-T}{(V2-V1)/V1}\right] + K \quad (1)$$

Where:
S = Strength
C and K = Constants

L=Load at the particular point in the paper measured by the load cell 98 as the system scans across the sheet of paper T=Average tension of the sheet of paper between roller 36 and roller 42

V2=Velocity of the sheet measured by the tachometer 104

V1=Velocity of the sheet as determined from the tachometer 60

In some cases, we have found that the calculation of strength can be simplified. In particular, if one desires to know the relative strength of the sheet at one point with respect to the strength at another point, without knowing the absolute value of the strength, it is unnecessary to measure the average tension T or the velocities V1 or V2. Rather, the only parameter necessary is the load, L, measured by the load cell 98. We have found that the relative strength of the paper can be determined simply from the relative loads, L, of the paper as measured by our system at various points on the sheet, according to the following equation:

$$\frac{S1}{S2} = \frac{KL1}{L2} \qquad (2)$$

Where:

S1 and S2 are strengths at two points

L1 and L2 are loads at the same two points

K is a constant

In some cases we have found that better results can be obtained by determining the strength based upon the load L and the velocity V2 according to the following equation:

$$S = LV2\,A + B \qquad (3)$$

Where:

S=Strength

L=Load

V2=Velocity

A and B=constants

In some cases we have found that better results can be determined by the utilization of the density, p, of the sheet as well as the load L and the velocity V2. In this case the appropriate equation is:

$$S = pLV2\,A2 + B2 \qquad (4)$$

Where:

The parameters are the same as above, and A2 and B2 are constants.

The density p in this case can be determined utilizing the conventionally measured parameters of basis weight divided by caliper. A conventional basis weight and sheet caliper measuring device used to determine density is shown schematically at reference numeral 101 in FIG. 1.

Figure 5:
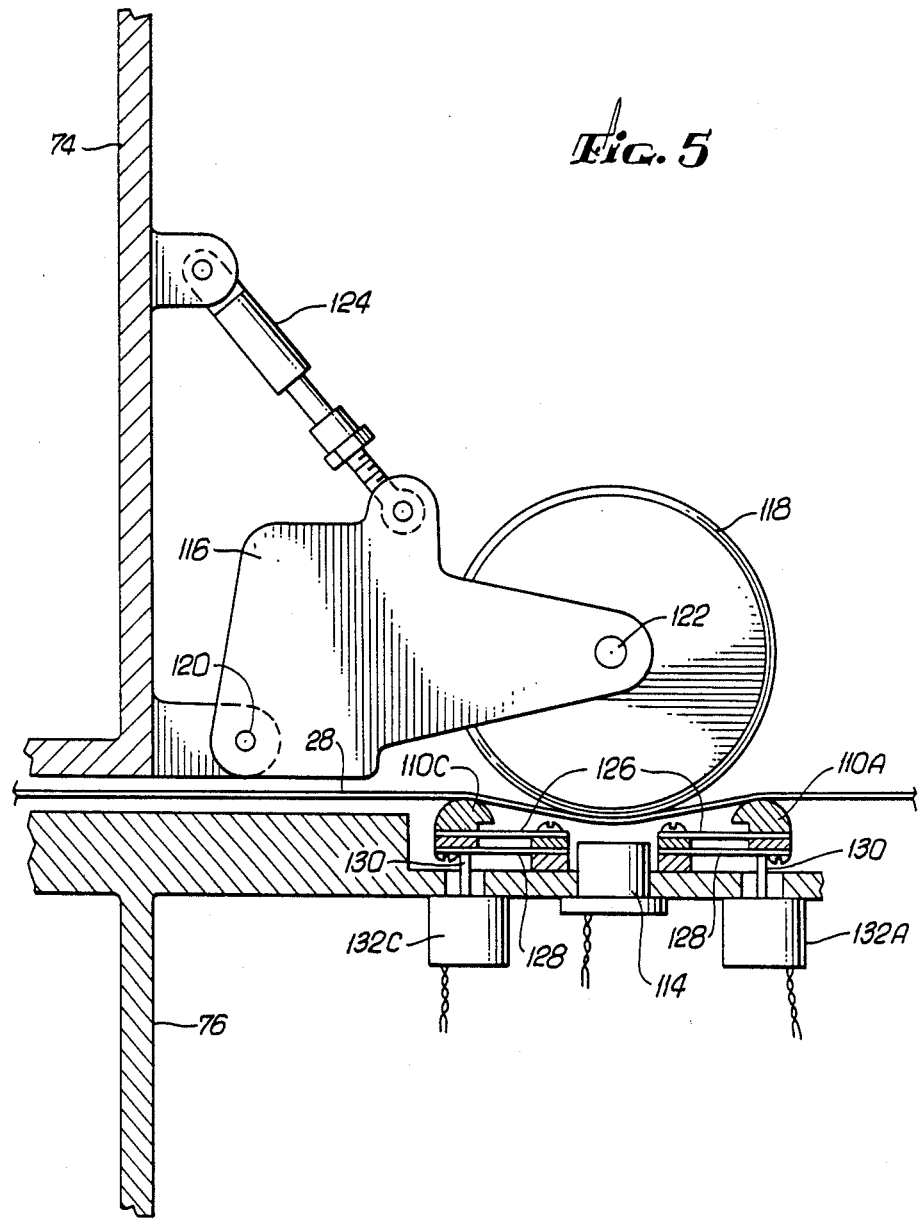
FIG. 5 is a partial cross-sectional side view of a sensor according to the present invention for sensing the "elastic modulus" of the paper.

FIG. 5 shows a partially sectioned side view of another embodiment of the sensor according to the present invention. Lower gauge support 76 supports a segmented horizontal ring 110 whose top surface is preferably aligned with the paper web 28. While a ring such as ring 110 is a preferred method of support, other forms of contacting structures could be used which contact the paper 28 in the vicinity of a central unsupported region.

It is within the broad scope of the invention to employ a sensor without a contact means such as ring 110. For example, this is possible where the sheet 28 is supported by processing equipment, such as a pair of rolls (see, e.g., rolls 52 and 66 of FIG. 1), and the sensor is positioned so as to be at a location where the movement of the sheet 28 is relatively stable. In such a variation of the invention in a particular application a tension correcting signal to correct for variations in the tension applied to particular segments of the sheet being monitored by the sensor would be utilized as may be required. (Such an alternative could employ a sensor substantially similar to that shown in FIG. 9 (discissed below) but without the ring 110'. (The sheet deflection sensor 114 may be included or omitted.)

Notwithstanding such alternative, the strength sensor shown in FIG. 5 provides specific advantages such as a stable signal relatively directly related to strength of the sheet material. Such a sensor, unlike the sensor of FIGS. 3-4, also facilitates a separate strength determination in the cross-direction and machine direction and minimizes the need for tension correcting signals in certain circumstances Upper gauge support 74 carries a first means such as the pressure wheel assembly which is comprised of bracket 116 and wheel 118. Pin 120 allows the wheel 118 freedom to move up and down while bearings (not shown) on axle 122 permit the wheel 118 to rotate freely. Up and down motion of the wheel 118 is controlled by air cylinder 124. In its extended position, air cylinder 124 positions the lower portion of the periphery of wheel 118 a fixed distance below the top surface of ring 110 and the sheet 28 and the ring 110 are in a cooperative relationship. For purposes of example, and not by way of limitation, if the diameters of wheel 118 and ring 110 are each about 5 inches, a satisfactory position for the lowest point on wheel 118 may be ¼ inch below the top surface of ring 110. It is also possible to invert the components as shown in FIG. 5, so that the ring 110 is above the sheet 28 and the wheel 118 is below the sheet 28. In a present form of the invention the components are so arranged.

The periphery of wheel 118 is preferably not cylindrical but, rather, is preferably approximately spherical. That is, the radius R as shown in FIG. 7 is preferably approximately equal to one-half the wheel diameter. Retraction of air cylinder 124 moves wheel 118 out of the way so that a web of paper 28 can be fed through the scanning station 62 easily upon initial set up. During operation, air cylinder 124 is extended and the sheet 28 is acted upon to move from a normal path to a deflected path in the strength sensor.

It will be understood by those skilled in the art that while a free running wheel for the purpose of deflecting the paper 28 below the top surface of ring 110 is disclosed herein, other structures can be utilized to accomplish the same function.

FIG. 6 is a top plan view of the portion of the lower gauge support member which supports the segmented ring 110A–D. Referring to both FIGS. 5 and 6, it can be seen that the ring 110 is comprised of four segments, 110A, 110B, 110C and 110D which are each supported by a pair of spaced leaf springs 126 and 128. The leaf springs 126, 128 constrain the segments 110A, 110B, 110C and 110D to move with straight line vertical motion. Linkage pins 130 couple each segment to load cells 132A, 132B, 132C and 132D which provide outputs that are a function of the paper force on the ring segments 110A, 110B, 110C and 110D. The force exerted on each of the segments 110A, 110B, 110C and 110D is a function of several factors including the tension on the sheet 28, the elastic modulus of the paper, the bending stiffness of the paper, and the physical dimensions of the gauging components. The modulus of elasticity and the bending stiffness of the paper may be different in the machine direction as compared to the cross direction, so that the force applied to load cells 132A and 132C is not necessarily the same as the force applied to load cells 132B and 132D. The difference in tension between the machine direction and the cross-direction also results in the difference in force.

Machine rigidity is an important factor in maintaining accuracy of measurement. In particular, it is important that the lowest point on the periphery of wheel 118 be maintained at a constant distance below the top surface of ring 110. If the mechanical rigidity of the structure is such that the spacing cannot be maintained, sensing means can easily be adapted to sense the relative positions of wheel 118 and ring 110, and to apply a correction to the strength equation to account for variations. A conventional sensor for this purpose is shown diagrammatically in FIG. 5 identified by the numeral 114. The output of displacement sensor 114, designated as "Z", provides a signal dependent on the deviation in the relative positions of wheel 118 and ring 110 from nominal, and may be used to modify the strength equation We have found that by properly combining the outputs of load cells 132A-132D it is possible to make a determination, on line, which accurately correlates with the standard "Mullen" test. In order to make such a determination, the outputs of load cells 132A-132D are fed to a computer 134 (FIG. 8) along with the output of the displacement sensor 114 (Z). The computer 134 calculates the "Mullen" strength. A presently preferred equation which may be used to determine strength is:

$$S_{mu} = A\left[\frac{L_a + L_c}{(C + Z)(T + F)}\right]^H + B\left[\frac{L_b + L_d}{(D + Z)(T + G)}\right]^J + E \quad (5)$$

Where
$S_{mu}$ is the "Mullen" strength of the paper;
A, B, C, D, E, F, G, H, and J are constants;
$L_a$, $L_b$, $L_c$, and $L_d$ are output signals from load sensors 132A through 132D, respectively;
T is a number representative of the tension in the web; and
Z is the output of displacement sensor 114.

If the gauge support members are held with adequate rigidity so that there is a sufficiently small relative motion between members 74 and 76, sensor 114 would not be needed, and the terms (C+Z) and (D+Z) could be replaced with constants. Similarly, if tension in the web does not vary significantly, the terms (T+F) and (T+G) could be replaced by constants. Thus, if in a particular installation the variations due to lack of rigidity and variations in tension are low enough, equation (5) could have the following form:

$$S_{mu} = A\left[\frac{L_a + L_c}{C}\right]^H + B\left[\frac{L_b + L_d}{D}\right]^J + E \quad (5a)$$

The values of the constants in equations (5) and (5a) will, of course, depend on the particular installation and the circumstances. They are empirically determined, and will, in general, be different as used in equation (5) as compared to (5a). The use of exponents H and J is not intended to indicate a value of necessarily different from 1. In some cases, depending on the installation and circumstances, one or both of these exponents may be 1. In addition, the constants may be found to be truly constant (within the desired accuracy of measurement) only if the process variations are relatively small, i e., within the ranges normally occurring during the manufacture of a single grade of paper. Unusually large variations in one or more of the process variables may require that one or more of the equation "constants" be adjusted to account for the variation.

Figure 11:
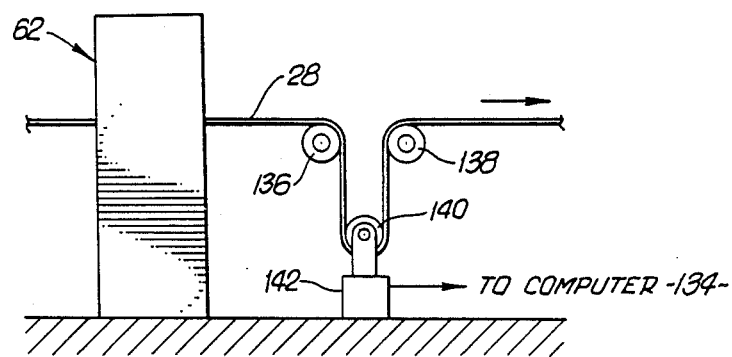
FIG. 11 is a schematic side view of one means for providing a signal responsive to web tension.

There are many ways known in the art for providing a signal to computer 134 which is a function of the tension in the web 28. One such system is shown schematically in FIG. 11. As shown, the web 28 is threaded around three rollers 136, 138 and 140. Rollers 136 and 138 are fixed relative to the papermaking machine and roller 140 is restrained from moving in a vertical direction by force transducer 142. The output of force transducer 142 will be a function of the tension of web 28 and can be used to provide the quantity T.

While the above equations provide strength value which correlate with the "Mullen" strength, as noted, it will be evident to those skilled in the art that it is possible to obtain other numbers which are also representative of strength using the strength sensor outputs in connection with different equations, even though such other numbers may not correlate with "Mullen".

For example, if a determination of machine direction and/or cross direction tensile strength is desired, equations in the following forms could be used:

$$S_{md} = A\left[\frac{L_a + L_c}{(C + Z)(T + F)}\right]^H + E \quad (6)$$

and $$S_{cd} = B\left[\frac{L_b + L_d}{(D + Z)(T + G)}\right]^J + E \quad (7)$$

where
$S_{md}$ and $S_{cd}$ are the machine direction and cross direction tensile strengths, respectively, and
the other terms are as previously defined By proper choice of the constants, equations (6) and (7) can provide determinations which correlate well with standard tensile tests While the same letters (A, B, C, etc.) are used in equations 5, 5a, 6 and 7 to represent constants, it should not be assumed that the constants as used in these equations necessarily have the same values. As noted above, the actual values of the constants will depend on the particular installation and circumstances. The comments above concerning modification of equation (5) on account of the effects of rigidity and tension are also applicable to equations (6) and (7) and similar simplified equations can be used if rigidity and/or tension variations are small enough. That is, the terms in the denominator of the first term of the equations could be replaced by a constant.

Figure 9:
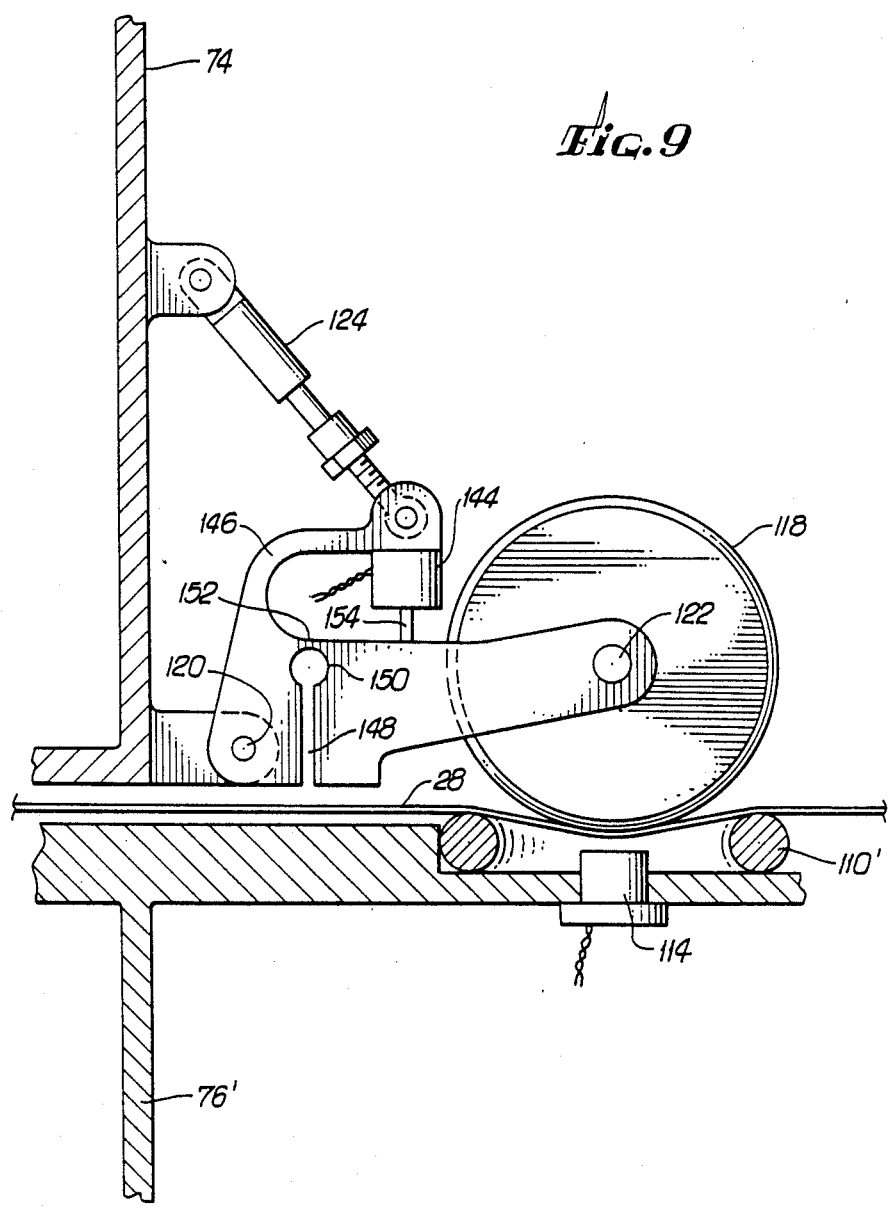
FIG. 9 is a partial cross-sectional side view of another embodiment of an "elastic modulus" sensor of the present invention.

A partial cross section view of another type of sensor suitable for use in the invented system is shown in FIG. 9. The main difference between the sensor of FIG. 9 and that shown in FIGS. 5 and 6 is that only a single load cell 144 is used, which provides an output representative of the force between wheel 118 and sheet 28 rather than the forces between sheet 28 and each of the segments of ring 110. In this sense the embodiment illustrated in FIG. 9 is similar to the embodiment of FIGS. 3-4.

In the embodiment of FIG. 9, since no instrumentation of the ring is required, an unsegmented ring 110' may be used solidly mounted to gauge carrier 76'. Bracket 146 is similar to bracket 116 except that it is cut out to receive load cell 144 and is made deformable by slot 148 and bore 150 which leaves a thin flexible web 152 The force acting between the sheet 28 and wheel 118 is thus sensed by load cell 144 through linkage pin 154.

Using the sensor of FIG. 9, a strength determination which can be correlated with the "Mullen" test can be obtained using the following equation $$S_{mu} = A\left[\frac{L_e}{(C+Z)(T+F)}\right]^H + E \tag{8}$$

where $L_e$ is the load on load cell 144; and the other terms are as previously defined An equation similar to Equation 8 can also be used in conjunction with the sensor of FIG. 5, where $L_e$ is the load on one of the transducers 132 or an average or sum of the outputs of two or more.

If the machine rigidity and/or variations in tension are low enough for the accuracy required, the terms $(C+Z)$ and/or $(T+F)$ can be replaced with constants, resulting in the following equation:

$$S = A\left[\frac{L}{C}\right]^H + E \tag{8a}$$

Where
S is a measure of the strength of the sheet;
L is the load on the load cell(s) used; and
A, C, E, and H are constants.

For optimum accuracy, under some circumstances it has been found desirable to modify the strength values as determined by equations 5-8. In particular, variations in basis weight and density can be the source of inaccuracy in the results obtained and one form of modified equation which may be used to obtain more accurate results is:

$$S_{corr} = K(\ln(BW)) + M(d-d_o)^N + S_{meas} \tag{9}$$

Where
$S_{meas}$ is the strength as determined from equations 5-8;
$S_{corr}$ is the corrected strength value;
$\ln(BW)$ is the natural logarithm of the basis weight of the sheet;
d and $d_o$ are the actual and nominal densities of the sheet; and
K, M, and N are constants.

Figure 10:
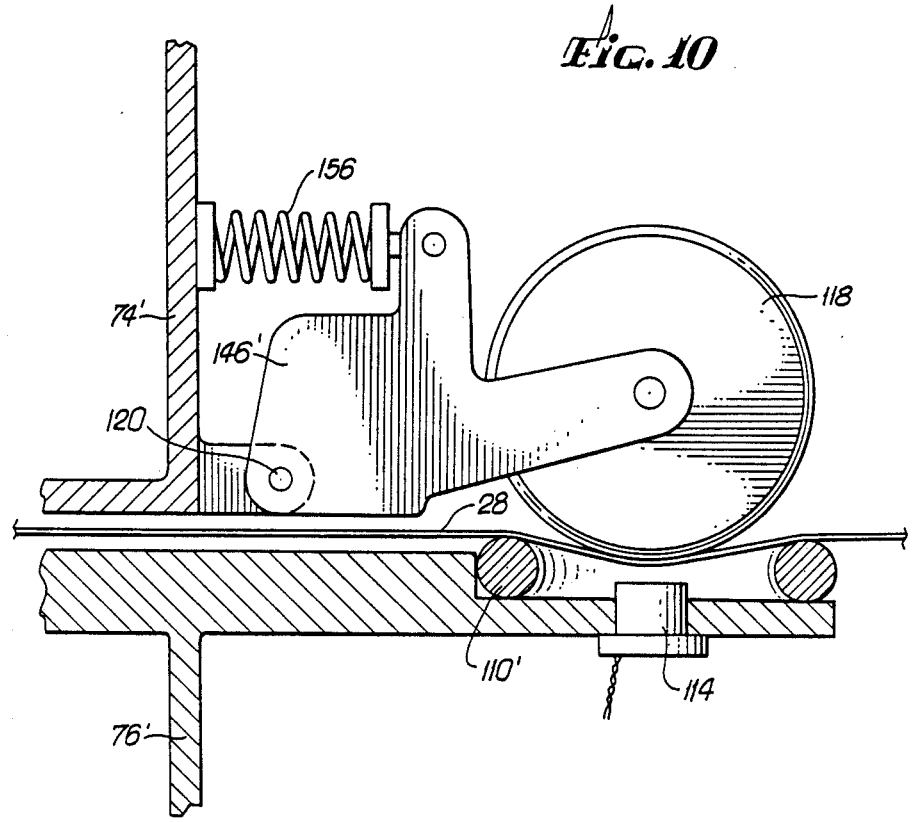
FIG. 10 is a partial cross-sectional side view of yet another embodiment of an "elastic modulus" sensor of the present invention.

The foregoing equations relate to embodiments of the invention wherein the load cell type of sensor is employed. As mentioned it is within the broad scope of the invention to employ other related sensors that provide a signal representative of a physical characteristic which may be correlated to physical strength of the sheet material. Detecting the deflection of the sheet material loaded by the relatively constant force (e.g., the weight of wheel 118) will provide such a signal. In the previously described embodiments of the invention, the sheet material is deformed a predetermined amount and the forces involved are sensed. In the sensor arrangement of this alternative system, a relatively constant force is applied to the sheet material and the resulting deflection of the sheet is sensed and processed to determine strength. For example, the sensor could be substantially similar to that shown in FIG. 9 with the component 144 omitted. The weight of the wheel (as is or with added weight) could provide a constant force that deflects the sheet material. The resulting deflection is measured by the sensor 114. Other force applying devices could be utilized such as springs or electronically controlled actuators. A diagrammatic side view of a sensor according to the embodiment just described is shown in FIG. 10. Spring 156 provides a downward force on the sheet in addition to that due to the weight of wheel 118. The strength of the sheet material, assuming a relatively constant sheet tension, may be determined by an equation of the form of:

$$S = AZ^H + E \tag{6}$$

where, A, E and H are constants and Z is the relevant deflection. With a deflection sensor employed, it is possible to employ a sensor with ring 110' or without such ring. Corrections to account for variations in tension and machine rigidity can be made as discussed in connection with the first sensor embodiment described.

It is also within the scope of the invention to employ both a force sensor and a deflection sensor. The resulting strength determinations could be combined or averaged or the signals resulting from the sensors could be employed in a modified equation.

What has been disclosed are various systems and methods for determining the strength of a sheet of paper which are nondestructive and which can be used "on line" to assure that paper being manufactured meets the required strength specification. Various adaptions and modifications of the invention will no doubt occur to those skilled in the art, and such adaptations and modifications within the spirit of the appended claims are intended to be covered thereby

We claim:

1. A system for determining a physical property of a moving sheet material, comprising:
a sheet support having a sheet support surface disposed to support the sheet at four sides of an unsupported region therebetween, the sheet support surface being adapted to nondestructively support the moving sheet; and
a sheet deflecting member disposed to nondestructively push the moving sheet into the unsupported region.

2. A system as in claim 1, wherein the sheet deflecting member is a rotatable wheel.

3. A system as in claim 2, further comprising a force detector operatively coupled to the wheel such that the force detector detects the force exerted by the wheel.

4. A system as in claim 1, wherein the sheet support surface defines a circular unsupported region.

5. A system as in claim 4, wherein the sheet support is a ring.

6. A system as in claim 1, further comprising a force detector operatively coupled to the sheet support such that the force detector detects the force of the sheet against the support surface.

7. A system as in claim 1, further comprising:
a force detector operatively coupled to the member such that the force detector detects the force exerted by the member; and
electronic circuits, operatively coupled to the detector, adapted to determine a physical characteristic of the sheet based upon the detected force.

8. A system as in claim 7, wherein the electronic circuits include a computer programmed to compute the physical characteristic.

9. A system as in claim 7, further comprising a sheet disposed between the sheet support and the member, wherein the physical characteristic is sheet failure strength.

10. A system as in claim 9, wherein the sheet is paper.

11. A system as in claim 1, further comprising:
a sheet deflection detector operatively coupled to the sheet support such that the detector detects the distance that the sheet is deflected into the unsupported region; and
electronic circuits, operatively coupled to the detector, adapted to determine a physical characteristic of the sheet based upon the detected deflection.

12. A system as in claim 11, wherein the electronic circuits include a computer programmed to compute the physical characteristic.

13. A system as in claim 11, further comprising a sheet disposed between the sheet support and the member, wherein the physical characteristic is sheet failure strength.

14. A system as in claim 13, wherein the sheet is paper.

15. A system as in claim 1, further comprising:
scanning means for scanning the sheet support and sheet deflecting member back and forth along a line perpendicular to the direction of motion of the sheet while the member is pushing the sheet into the unsupported region.

16. A system as in claim 1, wherein the sheet deflecting member is adapted to push against the sheet near the center of the unsupported region and over an area less than the entire unsupported region.

17. A system as in claim 1, further comprising a sheet moving between the sheet support and the sheet deflecting member, wherein the sheet deflecting member pushes against the sheet over an area smaller than the entire unsupported region, said area being centrally disposed with respect to the region.

18. A system for determining the failure strength of a sheet, comprising:
a physical deflecting means for exerting a deflecting force on a sheet to nondestructively deflect the sheet;
a detector for detecting a physical parameter related to the force exerted by the deflecting means and for producing signals in response thereto; and
electronic circuits, operatively coupled to the detector to receive the signals, wherein the circuits are adapted to determine the failure strength of the sheet based upon the signals.

19. A system as in claim 18, further comprising:
a sheet support defining an unsupported region within the support, wherein the support is arranged to be disposed on the side of the sheet opposite the physical deflecting means such that the sheet support will nondestructively support a portion of the sheet against the deflecting force and the deflecting means is operable to deflect the sheet into the unsupported region.

20. A system as in claim 19, wherein the sheet support is adapted to nondestructively support the sheet against the deflecting force while the sheet is moving.

21. A system as in claim 20, wherein the physical deflecting means includes a member adapted to nondestructively push against the sheet.

22. A system as in claim 21, wherein the member includes a sheet deflecting surface adapted for forceable contact with the sheet.

23. A system as in claim 22, wherein the member includes a wheel.

24. A system as in claim 22, wherein the sheet deflecting surface contacts the sheet over an area less than the entire unsupported region, said area of contact being centrally disposed with respect to the region.

25. A system as in claim 24, wherein the sheet is paper.

26. A system as in claim 22 wherein the sheet is moving, further comprising means for scanning the sheet deflecting member and sheet support back and forth along a line perpendicular to the direction of motion of the sheet.

27. A system as in claim 21, wherein the sheet support defines a circular unsupported region.

28. A system as in claim 21, wherein the detector includes a force detector and the physical parameter is the force exerted by the member on the sheet.

29. A system as in claim 28, wherein the sheet is moving, the system further comprising velocity means for determining the velocity of the deflected sheet, wherein the electronic circuits are operatively coupled to the velocity means and the circuits are adapted to determine the failure strength of the sheet based upon the determined sheet velocity and the force signals.

30. A sheet as in claim 29, further comprising density means for sensing the density of the sheet, wherein the electronic circuits are operatively coupled to the density means and the circuits are adapted to determine the failure strength of the sheet based upon the sensed sheet density, determined sheet velocity and the force signals.

31. A system as in claim 29, wherein the velocity means determines the velocities of the sheet within the unsupported region and outside of the unsupported region, the system further comprising tension means for sensing the tension in the sheet at a location outside the unsupported region, and wherein the electronic circuits are adapted to determine the failure strength of the sheet based upon the determined sheet velocities, sensed tension and the force signals.

32. A system as in claim 21, wherein the detector includes a sheet deflection detector and the physical parameter is a distance the sheet is deflected by the member.

33. A system as in claim 21, wherein the sheet is paper.

34. A system as in claim 21, wherein the system further comprises tension means for detecting the sheet tension in a sheet segment including the deflected sheet portion, and wherein the tension means is operatively coupled to the electronic circuits and the circuits are adapted to determine the failure strength of the sheet based upon the detector signals and the detected sheet tension.

35. A system as in claim 34, wherein the tension means detects the average sheet tension across the width of the sheet.

36. A system as in claim 18, wherein the electronic circuits include a computer programmed to compute the sheet failure strength.

37. A method for determining the failure strength of a sheet, comprising the steps of:
supporting one side of the sheet at a plurality of locations defining an unsupported region therebetween;
nondestructively pushing against the opposite side of the sheet such that a portion of the sheet is deflected into the unsupported region;
detecting a physical parameter related to the force exerted to deflect the sheet into the unsupported region; and
determining the failure strength of the sheet based upon the detected physical parameter.

38. A method as in claim 37, wherein the pushing step includes the step of forcing a sheet deflecting member against the opposite side of the sheet.

39. A method as in claim 38, further comprising the step of moving the plurality of sheet support locations along the plane of the sheet while nondestructively pushing against and supporting the deflected sheet on opposite sides thereof.

40. A method as in claim 39, wherein the detected physical parameter is the pushing force exerted to deflect the sheet.

41. A method as in claim 39, wherein the detected physical parameter is a distance the sheet is deflected into the unsupported region.

42. A method as in claim 34, wherein the sheet is paper.

43. A method as in claim 37, wherein the unsupported region is circular.

44. A method as recited in claim 37, further comprising the step of obtaining a corrected failure strength value utilizing the equation:

$$S_{corr} = K(\ln(BW) + M(d-d_o)^N + S$$

where
S is the failure strength value determined based upon the detected physical parameter,
$S_{corr}$ is the corrected failure strength value,
ln (BW) is the nature logarithm of the basis weight of the sheet, d and $d_o$ are, respectively, the actual and nominal densities of the sheet, and
K, M and N are constants.

45. A method for determining a physical property of a moving sheet material, comprising the steps of:
supporting one side of the sheet at a plurality of locations defining a circular unsupported region therebetween;
moving the sheet along the plane defined by the plural locations; and
nondestructively deflecting the moving sheet into the unsupported region while the sheet is moving.

46. A method as in claim 45, wherein the deflecting step includes the step of pushing against the opposite side of the sheet.

47. A process for indicating the failure strength of a sheet which is being drawn between a first and a second sheet support, wherein both supports are disposed adjacent to one side of the sheet, the process comprising the steps of:
while the sheet is moving, detecting a nondestructive deflecting load exerted against the opposite side of the sheet on a portion of the sheet between the first and second sheet supports; and
computing the failure strength of the sheet portion based upon the detected deflecting load.

48. A process according to claim 47, wherein the deflecting load is exerted against the sheet at a plurality of localized areas, and the deflecting load deflects the sheet a predetermined distance normal to the surface of the sheet within each of said localized areas.

49. A paper sheet strength sensor system, comprising:
a sheet support having at least one sheet supporting surface and defining an unsupported region;
a moving paper sheet having one side thereof supported by the at least one sheet supporting surface;
deflecting means for applying a deflecting force to unsupported portions of the other side of the moving sheet such that the sheet is forced against the at least one sheet supporting surface and deflected into the unsupported region, and for producing a force signal indicative of the magnitude of the deflecting force; and
computing means for receiving the force signal and using the force signal to compute the failure strength of the deflected portions of the paper sheet 50. A sheet strength sensor system, comprising:
a moving sheet;
a sheet support having a sheet supporting surface adjacent to one side of the moving sheet;
deflecting means for applying a deflecting force to unsupported portions of the opposite side of the moving sheet and producing force signals indicative of the magnitude of the deflecting force at a plurality of the unsupported sheet portions; and
computing means for receiving the force signals and using the force signals to compute the failure strength of a deflected portion of the sheet relative to the strength of at least one other sheet portion 51. A method for determining the failure strength of a moving sheet of material along a predetermined direction, comprising the steps of:
supporting the sheet on two spaced sheet supports, the supports being disposed, relative to each other, along the predetermined direction and defining an unsupported region therebetween;
deflecting a portion of the sheet into the unsupported region;
determining the force of the sheet on at least one of the supports;
determining the tension of the sheet in a sheet segment including the deflected portion;
computing the sheet failure strength along the predetermined direction using the equation:

$$S = A\left(\frac{L}{f}\right)^H + E$$

where
S is a value representative of sheet failure strength along the predetermined direction,
L is the force of the sheet against at least one of the sheet supports,
f is a function of the determined sheet tension, and
A, E and H are constants.

52. The method of claim 51, further comprising the step of determining the amount of deflection of the sheet, wherein f is a function of both the determined sheet tension and the amount of sheet deflection.

53. The method of claim 52, wherein $f=(C+Z)(T+F)$, where
T is a number representative of the determined sheet tension,
Z is a number representative of the amount of sheet deflection, and
C and F are constants.

54. A method for determining the failure strength of a moving sheet of material, comprising the steps of:
supporting the sheet on four sheet supports defining an unsupported region therebetween,
a first pair of supports disposed on opposite sides of the unsupported region along a first line, the second pair of supports being disposed on opposite sides of the unsupported region along a second line perpendicular to the first line;
deflecting a portion of the sheet into the unsupported region;
determining the force of the sheet on at least one sheet support of each of the first and second pair of sheet supports;
determining the tension of the sheet in an area of the sheet including the deflected portion;
computing the sheet strength using the equation:

$$S = A\left[\frac{L_1}{f_1}\right]^H + B\left[\frac{L_2}{f_2}\right]^J + E$$

where
S is a value representative of sheet failure strength,
$L_1$ the force of the sheet against at least one of the first pair of sheet supports,
$L_2$ is the force of the sheet against at least one of the second pair of sheet supports,
$f_1$ and $f_2$ are functions of the determined sheet tension, and
A, B, E, H and J are constants.

55. The method of claim 54, wherein $f_1=C(T+F)$ and $f_2=D(T+G)$ where
T is a number representative of the determined sheet tension and C, F, D and G are constants.

56. The method of claim 54 further comprising the step of determining the amount of deflection of the sheet, wherein $f_1=(C+Z)(T+F)$ and $f_2=(D+Z)(T+G)$ where
T is a number representative of the determined sheet tension, Z is a number representative of the amount of sheet deflection, and C, F, D and G are constants.

* * * * *